United States Patent [19]

Bewicke

[11] Patent Number: 5,820,867
[45] Date of Patent: Oct. 13, 1998

[54] GENERAL ANTI-DEPRESSANT COMPOSITION FOR DIETARY SUPPLEMENT

[76] Inventor: Calverly M. Bewicke, 1423 Butterfield Rd., San Anselmo, Calif. 94960

[21] Appl. No.: 847,367

[22] Filed: Apr. 24, 1997

[51] Int. Cl.⁶ ..................................................... A61K 35/78
[52] U.S. Cl. ....................... 424/195.1; 514/249; 514/261; 514/345; 514/474
[58] Field of Search ........................................... 424/195.1

[56] References Cited

U.S. PATENT DOCUMENTS 4,973,467  11/1990  Sahley ................................... 424/195.1
5,569,458  10/1996  Greenberg ............................. 424/195.1

OTHER PUBLICATIONS

CA 119: 85914.

*Primary Examiner*—Amelia Owens
*Attorney, Agent, or Firm*—Benman & Collins

[57] ABSTRACT

A novel dietary supplement composition is provided that serves as a general anti-depressant. The dietary supplement employs an extract of St. John's Wort and additionally includes an extract of *Ginkgo biloba,* Vitamin B6, Vitamin B12, Folic acid, and Vitamin C.

6 Claims, No Drawings

GENERAL ANTI-DEPRESSANT COMPOSITION FOR DIETARY SUPPLEMENT

TECHNICAL FIELD

The present invention relates generally to dietary supplements, and, more particularly, to a special blend of St. John's Wort herb extract formulated with other herbal extracts, vitamins and minerals, when taken over a period of time, to improve mental well-being and mental acuity and to assist in relief of depression.

BACKGROUND ART

Throughout history, humans have ingested and otherwise consumed a wide variety of substances to relieve depression and increase mental acuity. Examples of such substances include prescription drugs, such as many brands of tricyclic anti-depressants, Prozac, and other stimulants. However, many such substances have undesirable side-effects such as nausea, insomnia, and other problems. A significant number of patients (estimated between 17% and 30%) have to discontinue the use of prescription anti-depressants because of these effects.

One anti-depressant substance which does not typically exhibit any significant side effects is an extract from St. John's Wort (*Hypericum perforatum*). Another substance which has been demonstrated to increase mental acuity (particularly in the elderly), and to relieve depression, is an extract from the leaf of the Ginkgo tree (*Ginkgo biloba*). Additionally, people suffering from depression are often found to be deficient in certain key vitamins, namely, Folic acid, Vitamin B6, and Vitamin B12. Below is a summary of the qualities of the above mentioned substances, and a description of their significance to this particular invention:

St. John's Wort Extract

St. John's Wort has been in use for centuries in the field of traditional herbal medicine. In recent years, the plant has been scientifically scrutinized, and a number of its key chemical constituents have been identified. These include a volatile oil, a resin, a tannin, glycosides of stearic, palmic, and myric acids, and hypercin. Modern scientifically calibrated extracts are made containing guaranteed levels of one of the constituents, Hypericin, at concentrations between 0.1% to 0.3% by weight. Studies have shown that use of specific amounts of these extracts, when taken over a period of time (two weeks or more), provide relief from depression in a high percentage of individuals, without causing the negative side effects often found when prescription drugs are used.

Today, St. John's Wort extract is widely available in Germany and other European countries as an herbal supplement, which is widely prescribed by doctors and health practitioners. The quantity that is generally recommended for use is an amount of the extract equivalent to 1 mg of Hypericin per tablet or capsule. The recommended dosage is three such tablets/capsules per day.

Given the well-established, beneficial effects of St. John's Wort extract in conditions where depression exists, and the rare incidence of associated side effects, it would be desirable to provide the St. John's Wort extract in a dietary supplement improved over that already commercially available. Such a dietary supplement should enhance the general anti-depressant qualities offered by the St. John's Wort extract without introducing any harmful side effects. It should be inexpensively manufactured, and comply with all applicable government regulations.

DISCLOSURE OF INVENTION

In accordance with the present invention, a dietary supplement is provided that comprises St. John's Wort extract combined with another herbal extract and certain vitamins. The present supplement therefore enhances the general relaxation achieved from the consumption of St. John's Wort extract alone.

BEST MODES FOR CARRYING OUT THE INVENTION

Reference is now made in detail to a specific embodiment of the present invention, which illustrates the best mode presently contemplated by the inventor for practicing the invention. Alternative embodiments are also briefly described as applicable.

The dietary supplement of the invention comprises St. John's Wort extract, one other herbal extract, and a combination of certain vitamins. The dietary supplement composition is preferably put into a tablet using known technology, such that the daily dose for an adult would be three tablets.

The St. John's Wort extract employed in the practice of the present invention is of a pharmaceutical grade that is commercially available from several European manufacturing sources. It is preferably standardized for Hypericin content to contain 0.3 wt %.

In addition to St. John's Wort extract, the present dietary supplement contains one other complementary herbal extract and four vitamins to provide benefits that enhance the nutritional quality of the St. John's Wort extract.

Each tablet of the invention contains the following ingredients, within the following ranges: (a) about 200 to 400 mg of the St. John's Wort Extract (0.3% Hypericin); (b) about 30 to 50 mg of *Ginkgo biloba* extract, standardized to contain 24% Ginkgoflavoneglycosides and 6% Terpene lactones; (c) about 20 to 40 mg of Vitamin B6; (d) about 250 to 350 mcg of Vitamin B12; (e) about 83 to 133 mcg of Folic acid; and (f) about 150 to 250 mg of Vitamin C.

Ginkgo Biloba

*Ginkgo biloba* extract is also a pharmaceutical grade extract and contains a 100 times concentration of the leaves from the Ginkgo tree. This extract is standardized to contain exact amounts of certain key constituents, namely, 24% Ginkgoflavoneglycosides and 6% Terpene lactones. This type of Ginkgo extract has undergone very extensive testing, and has demonstrated a remarkable ability to improve mental acuity in people of all ages; this effect is most notable in older people, and in Europe, Ginkgo is considered to be the most effective treatment for the symptoms of senility. Several studies have also shown Ginkgo extract to be an effective anti-depressant, particularly in people over 40 years of age, and to enhance the effects of other anti-depressant medication.

Vitamin B6

Vitamin B6 levels are typically low in depressed patients, and some authorities go so far as to conclude that many cases of depression are simply as a result of low Vitamin B6 levels. Vitamin B6 has many functions in the brain, and is essential in the manufacture of monoamines. Typical effective dose range is 50 to 100 mg per day.

Folic acid and Vitamin B12

Folic acid and Vitamin B12 function together in many biochemical processes. Folic acid deficiency is the most common deficiency in the world, and studies of depressed patients show that as many as 31 to 35% are deficient in this vitamin. Vitamin B12 deficiency is less common, but can also cause depression, particularly in the elderly. Correcting these two deficiencies results in a dramatic improvement in mood.

Vitamin C

Vitamin C is essential for the optimal functioning of the body's immune system. This vitamin also performs many other essential functions in the body, and adequate supplies, in excess of the amount required to fulfill the USRDA are widely considered to lead to improved health and well-being.

In addition to the St. John's Wort extract, and other herbs and vitamins, the dietary supplement of the present invention may include magnesium and other excipeints commonly used in the commercial manufacture of tablets. These ingredients are considered to be inactive, in that they don't contribute to the effects of the formula, but are merely included as a part of the packaging or tableting process.

The most preferred composition of the present dietary supplement is as follows: (a) 300 mg of St. John's Wort extract; (b) 40 mg of *Ginkgo biloba* extract; (c) 30 mg of Vitamin B6; (c) 300 mcg of Vitamin B12; (d) 100 mcg of Folic acid; and (e) 200 to 250 mg of Vitamin C.

Thus there has been disclosed a dietary supplement comprising St. John's Wort, one other herbal extract and four vitamins. It will be readily apparent to those skilled in the art that various changes and modifications of an obvious nature may be made without departing from the spirit of the invention, and all such changes and modifications of an obvious nature may be made without departing from the spirit of the invention, and all such changes and modifications are considered to fall within the scope of the invention, as defined by the appended claims.

What is claimed is:

1. A dietary supplement comprising an extract of St. John's Wort, one other anti-depressant herbal extract, and four vitamins.

2. The dietary supplement of claim 1 wherein said St. John's Wort extract contains at least 0.3 wt % Hypericin.

3. The dietary supplement of claim 2 wherein said St. John's Wort extract is present in said dietary supplement within the range of 200 to 400 mg.

4. The dietary supplement of claim 1 wherein said one other herbal extract comprises *Ginkgo biloba* extract and wherein said four vitamins comprise Vitamin B6, Vitamin B12, Folic acid, and Vitamin C.

5. The dietary supplement of claim 1 comprising the following components:
   (a) about 200 to 400 mg of the St. John's Wort Extract (0.3 wt. % Hypericin;
   (b) about 30 to 50 mg of *Ginkgo biloba* extract, standardized to contain 24% Ginkgoflavoneglycosides and 6% Terpene lactones;
   (c) about 20 to 40 mg of Vitamin B6;
   (d) about 250 to 350 mcg of Vitamin B12;
   (e) about 83 to 133 mcg of Folic acid; and
   (f) about 150 to 250 mg of Vitamin C.

6. The dietary supplement of claim 5 comprising the following components
   (a) about 300 mg of the St. John's Wort Extract (0.3 wt. % Hypericin;
   (b) about 40 mg of *Ginkgo biloba* extract, standardized to contain 24% Ginkgoflavoneglycosides and 6% Terpene lactones;
   (c) about 30 mg of Vitamin B6;
   (d) about 300 mcg of Vitamin B12;
   (e) about 100 mcg of Folic acid; and
   (f) about 200 to 250 mg of Vitamin C.

* * * * *